United States Patent
Friedlander et al.

(10) Patent No.: US 8,968,197 B2
(45) Date of Patent: Mar. 3, 2015

(54) DIRECTING A USER TO A MEDICAL RESOURCE

(75) Inventors: Robert R. Friedlander, Southbury, CT (US); Richard Hennessy, Austin, TX (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 19 days.

(21) Appl. No.: 13/253,431

(22) Filed: Oct. 5, 2011

(65) Prior Publication Data
US 2012/0059227 A1 Mar. 8, 2012

Related U.S. Application Data

(63) Continuation-in-part of application No. 12/875,261, filed on Sep. 3, 2010, now Pat. No. 8,370,350.

(51) Int. Cl.
| | |
|---|---|
| *A61B 5/00* | (2006.01) |
| *G01C 21/20* | (2006.01) |
| *G01C 21/36* | (2006.01) |
| *A61B 5/11* | (2006.01) |
| *A61B 5/01* | (2006.01) |
| *A61B 5/0404* | (2006.01) |

(Continued)

(52) U.S. Cl.
CPC .............. *G01C 21/20* (2013.01); *A61B 5/0022* (2013.01); *G01C 21/3617* (2013.01); *A61B 5/1112* (2013.01); *A61B 5/01* (2013.01); *A61B 5/0404* (2013.01); *A61B 5/14532* (2013.01); *A61B 5/14551* (2013.01)
USPC .... 600/301; 701/515; 707/705; 707/E17.001; 707/94

(58) Field of Classification Search
CPC ...... A61B 5/0022; A61B 5/0024; A61B 5/01; A61B 5/02; G06F 17/30241; G06F 19/3418; G01C 21/3617
USPC ........... 600/301; 701/515; 707/705, E17.001, 707/941, 999.107
See application file for complete search history.

(56) References Cited

U.S. PATENT DOCUMENTS

| | | | | | |
|---|---|---|---|---|---|
| 2,671,443 | A | * | 3/1954 | Holland | 601/18 |
| 3,711,152 | A | * | 1/1973 | Sirpak et al. | 297/282 |
| 4,803,625 | A | * | 2/1989 | Fu et al. | 600/483 |

(Continued)

OTHER PUBLICATIONS

NIH article, "AgePage—Hyperthermia: Too Hot to Your Health", Published on Jul. 2010, 3 pages, accessed online at <http://www.nia.nih.gov/health/publication/hyperthermia-too-hot-your-health> on Sep. 5, 2013.*

(Continued)

*Primary Examiner* — Phuong Thao Cao
(74) *Attorney, Agent, or Firm* — John R. Pivnichny; Law Office of Jim Boice

(57) ABSTRACT

A processor-implemented method, system, and/or computer program product directs a user using a physiological sensor to a needed medical resource. A real-time state of a medical condition of a user is determined based on readings from a physiological sensor on a user. A processing system correlates the real-time state of the medical condition of the user to a medical resource, which has been predetermined to have a capability of ameliorating the real-time state of the medical condition of the user. Directions are then sent, to the user, for a temporally nearest medical resource that has been predetermined to have the capability of ameliorating the real-time state of the medical condition of the user.

3 Claims, 3 Drawing Sheets

(51) Int. Cl.
*A61B 5/145* (2006.01)
*A61B 5/1455* (2006.01)

(56) References Cited

U.S. PATENT DOCUMENTS

| | | | |
|---|---|---|---|
| 4,883,063 A * | 11/1989 | Bernard et al. | 600/483 |
| 4,890,227 A | 12/1989 | Watanabe et al. | |
| 5,024,225 A * | 6/1991 | Fang | 600/301 |
| 5,070,453 A | 12/1991 | Duffany | |
| 5,111,391 A | 5/1992 | Fields et al. | |
| 5,128,871 A | 7/1992 | Schmitz | |
| 5,148,365 A | 9/1992 | Dembo | |
| 5,167,230 A * | 12/1992 | Chance | 600/323 |
| 5,216,593 A | 6/1993 | Dietrich et al. | |
| 5,590,648 A * | 1/1997 | Mitchell et al. | 600/301 |
| 5,601,435 A * | 2/1997 | Quy | 434/307 R |
| 5,764,740 A | 6/1998 | Holender | |
| 5,838,918 A | 11/1998 | Prager et al. | |
| 5,880,598 A | 3/1999 | Duong | |
| 6,021,403 A | 2/2000 | Horvitz et al. | |
| 6,049,776 A | 4/2000 | Donnelly et al. | |
| 6,076,166 A | 6/2000 | Moshfeghi et al. | |
| 6,102,856 A | 8/2000 | Groff et al. | |
| 6,144,837 A * | 11/2000 | Quy | 434/307 R |
| 6,164,975 A | 12/2000 | Weingarden et al. | |
| 6,212,524 B1 | 4/2001 | Weissman et al. | |
| 6,272,483 B1 | 8/2001 | Joslin et al. | |
| 6,289,340 B1 | 9/2001 | Puram et al. | |
| 6,321,207 B1 | 11/2001 | Ye | |
| 6,381,577 B1 * | 4/2002 | Brown | 705/2 |
| 6,449,641 B1 | 9/2002 | Moiin et al. | |
| 6,466,232 B1 * | 10/2002 | Newell et al. | 715/700 |
| 6,484,155 B1 | 11/2002 | Kiss et al. | |
| 6,578,068 B1 | 6/2003 | Bowman-Amuah | |
| 6,604,160 B1 | 8/2003 | Le et al. | |
| 6,647,374 B2 | 11/2003 | Kansal | |
| 6,675,159 B1 | 1/2004 | Lin et al. | |
| 6,885,936 B2 * | 4/2005 | Yashio et al. | 701/515 |
| 6,889,137 B1 * | 5/2005 | Rychlak | 701/410 |
| 6,905,816 B2 | 6/2005 | Jacobs et al. | |
| 6,937,147 B2 | 8/2005 | Dilbeck et al. | |
| 6,954,736 B2 | 10/2005 | Menninger et al. | |
| 7,149,533 B2 * | 12/2006 | Laird et al. | 455/456.3 |
| 7,181,428 B2 | 2/2007 | Lawrence | |
| 7,213,009 B2 | 5/2007 | Pestotnik et al. | |
| 7,221,928 B2 * | 5/2007 | Laird et al. | 455/404.1 |
| 7,243,024 B2 * | 7/2007 | Endicott | 701/440 |
| 7,295,925 B2 | 11/2007 | Breed et al. | |
| 7,319,386 B2 * | 1/2008 | Collins et al. | 340/539.12 |
| 7,343,316 B2 | 3/2008 | Goto et al. | |
| 7,400,257 B2 * | 7/2008 | Rivas | 340/573.1 |
| 7,403,922 B1 | 7/2008 | Lewis et al. | |
| 7,457,764 B1 | 11/2008 | Bullock et al. | |
| 7,460,019 B2 | 12/2008 | Henderson | |
| 7,464,147 B1 | 12/2008 | Fakhouri et al. | |
| 7,516,142 B2 | 4/2009 | Friedlander et al. | |
| 7,523,118 B2 | 4/2009 | Friedlander et al. | |
| 7,539,533 B2 * | 5/2009 | Tran | 600/509 |
| 7,539,623 B1 * | 5/2009 | Wyatt | 705/5 |
| 7,542,878 B2 * | 6/2009 | Nanikashvili | 702/188 |
| 7,558,745 B2 | 7/2009 | Cullen et al. | |
| 7,584,160 B2 | 9/2009 | Friedlander et al. | |
| 7,630,948 B2 | 12/2009 | Friedlander et al. | |
| 7,630,986 B1 | 12/2009 | Herz et al. | |
| 7,647,288 B2 | 1/2010 | Friedlander et al. | |
| 7,693,736 B1 | 4/2010 | Chu et al. | |
| 7,702,605 B2 | 4/2010 | Friedlander et al. | |
| 7,739,606 B2 | 6/2010 | Sawada et al. | |
| 7,752,154 B2 | 7/2010 | Friedlander et al. | |
| 7,801,885 B1 | 9/2010 | Verma | |
| 7,930,262 B2 | 4/2011 | Friedlander et al. | |
| 7,933,228 B2 | 4/2011 | Coley | |
| 7,935,076 B2 * | 5/2011 | Estes et al. | 604/65 |
| 7,937,214 B2 * | 5/2011 | Kaneda et al. | 701/465 |
| 8,001,008 B2 | 8/2011 | Engle | |
| 8,010,516 B2 | 8/2011 | Ishii et al. | |
| 8,045,455 B1 * | 10/2011 | Agronow et al. | 370/229 |
| 8,055,603 B2 | 11/2011 | Angell et al. | |
| 8,204,779 B1 | 6/2012 | Hughes et al. | |
| 8,207,859 B2 * | 6/2012 | Enegren et al. | 340/573.1 |
| 8,207,860 B2 * | 6/2012 | Enegren et al. | 340/573.1 |
| 2001/0034362 A1 | 10/2001 | Ross et al. | |
| 2001/0039373 A1 * | 11/2001 | Cunningham et al. | 600/300 |
| 2001/0051765 A1 * | 12/2001 | Walker et al. | 600/300 |
| 2002/0019764 A1 | 2/2002 | Mascarenhas | |
| 2002/0035572 A1 * | 3/2002 | Takatori et al. | 707/104.1 |
| 2002/0052756 A1 | 5/2002 | Lomangino | |
| 2002/0059201 A1 | 5/2002 | Work | |
| 2002/0107824 A1 | 8/2002 | Ahmed et al. | |
| 2002/0111922 A1 | 8/2002 | Young et al. | |
| 2002/0115447 A1 | 8/2002 | Martin et al. | |
| 2002/0182573 A1 | 12/2002 | Watson | |
| 2003/0033180 A1 | 2/2003 | Shekar et al. | |
| 2003/0065544 A1 | 4/2003 | Elzinga et al. | |
| 2003/0088491 A1 | 5/2003 | Liu et al. | |
| 2003/0092976 A1 * | 5/2003 | Murase et al. | 600/300 |
| 2003/0097291 A1 | 5/2003 | Freedman | |
| 2003/0140063 A1 | 7/2003 | Pizzorno et al. | |
| 2003/0177038 A1 | 9/2003 | Rao | |
| 2003/0220830 A1 | 11/2003 | Myr | |
| 2003/0220860 A1 | 11/2003 | Heytens et al. | |
| 2004/0006694 A1 | 1/2004 | Heelan et al. | |
| 2004/0122787 A1 | 6/2004 | Avinash et al. | |
| 2004/0155772 A1 * | 8/2004 | Medema et al. | 340/539.12 |
| 2004/0155815 A1 * | 8/2004 | Muncaster et al. | 342/357.09 |
| 2004/0199056 A1 * | 10/2004 | Husemann et al. | 600/300 |
| 2004/0243422 A1 | 12/2004 | Weber et al. | |
| 2004/0267595 A1 | 12/2004 | Woodings et al. | |
| 2005/0004823 A1 | 1/2005 | Hnatio | |
| 2005/0004828 A1 | 1/2005 | DeSilva et al. | |
| 2005/0037730 A1 * | 2/2005 | Montague | 455/404.2 |
| 2005/0038608 A1 | 2/2005 | Chandra et al. | |
| 2005/0080806 A1 | 4/2005 | Doganata et al. | |
| 2005/0085257 A1 * | 4/2005 | Laird et al. | 455/550.1 |
| 2005/0101873 A1 * | 5/2005 | Misczynski et al. | 600/509 |
| 2005/0144062 A1 | 6/2005 | Mittal et al. | |
| 2005/0149466 A1 | 7/2005 | Hale et al. | |
| 2005/0165594 A1 | 7/2005 | Chandra et al. | |
| 2005/0198486 A1 | 9/2005 | Desmond et al. | |
| 2005/0222989 A1 | 10/2005 | Haveliwala et al. | |
| 2005/0240668 A1 | 10/2005 | Rolia et al. | |
| 2006/0010090 A1 * | 1/2006 | Brockway et al. | 706/46 |
| 2006/0023848 A1 * | 2/2006 | Mohler et al. | 379/41 |
| 2006/0031110 A1 | 2/2006 | Benbassat et al. | |
| 2006/0036560 A1 | 2/2006 | Fogel | |
| 2006/0069514 A1 | 3/2006 | Chow et al. | |
| 2006/0105830 A1 | 5/2006 | Nemitz et al. | |
| 2006/0118541 A1 * | 6/2006 | Ellis et al. | 219/217 |
| 2006/0155627 A1 | 7/2006 | Horowitz | |
| 2006/0184412 A1 | 8/2006 | Kagan et al. | |
| 2006/0194186 A1 | 8/2006 | Nanda | |
| 2006/0200435 A1 | 9/2006 | Flinn et al. | |
| 2006/0206724 A1 * | 9/2006 | Schaufele et al. | 713/186 |
| 2006/0208169 A1 * | 9/2006 | Breed et al. | 250/221 |
| 2006/0218010 A1 | 9/2006 | Michon et al. | |
| 2006/0226991 A1 * | 10/2006 | Rivas | 340/573.1 |
| 2006/0294058 A1 | 12/2006 | Rose et al. | |
| 2007/0073654 A1 | 3/2007 | Chow et al. | |
| 2007/0073754 A1 | 3/2007 | Friedlander et al. | |
| 2007/0073799 A1 | 3/2007 | Adjali et al. | |
| 2007/0112261 A1 * | 5/2007 | Enegren et al. | 600/365 |
| 2007/0112735 A1 | 5/2007 | Holloway et al. | |
| 2007/0124058 A1 * | 5/2007 | Kitagawa et al. | 701/200 |
| 2007/0150325 A1 | 6/2007 | Bjornson | |
| 2007/0168307 A1 | 7/2007 | Floudas et al. | |
| 2007/0174090 A1 | 7/2007 | Friedlander et al. | |
| 2007/0174091 A1 | 7/2007 | Friedlander et al. | |
| 2007/0174101 A1 | 7/2007 | Li et al. | |
| 2007/0179356 A1 * | 8/2007 | Wessel | 600/300 |
| 2007/0185737 A1 | 8/2007 | Friedlander et al. | |
| 2007/0203872 A1 | 8/2007 | Flinn et al. | |
| 2007/0244701 A1 | 10/2007 | Erlanger et al. | |
| 2007/0274337 A1 | 11/2007 | Purpura | |
| 2008/0015422 A1 * | 1/2008 | Wessel | 600/301 |

(56) References Cited

U.S. PATENT DOCUMENTS

| | | |
|---|---|---|
| 2008/0015871 A1 | 1/2008 | Eder |
| 2008/0028409 A1 | 1/2008 | Cherkasova et al. |
| 2008/0065576 A1 | 3/2008 | Friedlander et al. |
| 2008/0077463 A1 | 3/2008 | Friedlander et al. |
| 2008/0082356 A1 | 4/2008 | Friedlander et al. |
| 2008/0082374 A1 | 4/2008 | Kennis et al. |
| 2008/0147694 A1 | 6/2008 | Ernest et al. |
| 2008/0155104 A1 | 6/2008 | Quinn et al. |
| 2008/0167929 A1 | 7/2008 | Cao et al. |
| 2008/0172352 A1 | 7/2008 | Friedlander et al. |
| 2008/0177687 A1 | 7/2008 | Friedlander et al. |
| 2008/0177688 A1 | 7/2008 | Friedlander et al. |
| 2008/0189402 A1 | 8/2008 | Betzler et al. |
| 2008/0208801 A1 | 8/2008 | Friedlander et al. |
| 2008/0208813 A1 | 8/2008 | Friedlander et al. |
| 2008/0208814 A1 | 8/2008 | Friedlander et al. |
| 2008/0208832 A1 | 8/2008 | Friedlander et al. |
| 2008/0208838 A1 | 8/2008 | Friedlander et al. |
| 2008/0208875 A1 | 8/2008 | Friedlander et al. |
| 2008/0208901 A1 | 8/2008 | Friedlander et al. |
| 2008/0208902 A1 | 8/2008 | Friedlander et al. |
| 2008/0208903 A1 | 8/2008 | Friedlander et al. |
| 2008/0208904 A1 | 8/2008 | Friedlander et al. |
| 2008/0209493 A1 | 8/2008 | Choi et al. |
| 2008/0221419 A1* | 9/2008 | Furman .................. 600/324 |
| 2008/0242509 A1* | 10/2008 | Menektchiev et al. .......... 482/4 |
| 2008/0246629 A1* | 10/2008 | Tsui et al. ................ 340/870.07 |
| 2008/0275321 A1* | 11/2008 | Furman .................. 600/323 |
| 2008/0281974 A1 | 11/2008 | Slothouber et al. |
| 2008/0288862 A1 | 11/2008 | Smetters et al. |
| 2008/0294459 A1 | 11/2008 | Angell et al. |
| 2008/0294692 A1 | 11/2008 | Angell et al. |
| 2009/0024553 A1 | 1/2009 | Angell et al. |
| 2009/0069787 A1* | 3/2009 | Estes et al. .................... 604/503 |
| 2009/0089149 A1* | 4/2009 | Lerner et al. .................... 705/10 |
| 2009/0106179 A1 | 4/2009 | Friedlander et al. |
| 2009/0112670 A1 | 4/2009 | Black et al. |
| 2009/0138300 A1 | 5/2009 | Kagan et al. |
| 2009/0140923 A1* | 6/2009 | Graves et al. ................ 342/450 |
| 2009/0198696 A1* | 8/2009 | Banks .............................. 707/9 |
| 2009/0198733 A1* | 8/2009 | Gounares et al. .......... 707/104.1 |
| 2009/0267774 A1* | 10/2009 | Enegren et al. ............. 340/573.1 |
| 2009/0267775 A1* | 10/2009 | Enegren et al. ............. 340/573.1 |
| 2009/0270705 A1* | 10/2009 | Enegren et al. ............... 600/365 |
| 2009/0287503 A1 | 11/2009 | Angell et al. |
| 2009/0287674 A1 | 11/2009 | Bouillet et al. |
| 2009/0287683 A1 | 11/2009 | Bennett |
| 2009/0299766 A1 | 12/2009 | Friedlander et al. |
| 2009/0299928 A1 | 12/2009 | Kongtcheu |
| 2010/0010832 A1* | 1/2010 | Boute et al. ........................ 705/3 |
| 2010/0042456 A1 | 2/2010 | Stinchcombe et al. |
| 2010/0056643 A1* | 3/2010 | Bachynsky et al. ........... 514/728 |
| 2010/0057655 A1* | 3/2010 | Jacobson et al. ................ 706/45 |
| 2010/0063877 A1 | 3/2010 | Soroca et al. |
| 2010/0077438 A1 | 3/2010 | Ansari |
| 2010/0131028 A1* | 5/2010 | Hsu et al. ......................... 607/42 |
| 2010/0191516 A1 | 7/2010 | Benish et al. |
| 2010/0223581 A1 | 9/2010 | Manolescu et al. |
| 2010/0228715 A1 | 9/2010 | Lawrence |
| 2011/0054968 A1 | 3/2011 | Galaviz |
| 2011/0093287 A1* | 4/2011 | Dicks et al. ......................... 705/2 |
| 2011/0190579 A1* | 8/2011 | Ziarno et al. .................. 600/109 |
| 2011/0246055 A1* | 10/2011 | Huck et al. ..................... 701/201 |
| 2011/0251790 A1* | 10/2011 | Liotopoulos et al. .......... 701/209 |
| 2011/0275480 A1* | 11/2011 | Champsaur ........................ 482/4 |
| 2011/0275907 A1* | 11/2011 | Inciardi et al. ................ 600/301 |
| 2012/0108984 A1* | 5/2012 | Bennett et al. ................ 600/485 |
| 2012/0245479 A1* | 9/2012 | Ganesh et al. ................ 600/508 |
| 2013/0096966 A1* | 4/2013 | Barnes, Jr. ......................... 705/5 |
| 2013/0109997 A1* | 5/2013 | Linke et al. ................... 600/549 |

OTHER PUBLICATIONS

Mordecai M., "Physiological stats monitoring for firefighters: Watching out for overexertion before its too late", Jun. 18, 2008, 4 pages, accessed online at <http://expoweb2:8011/webapps/ExtJs/palm/palmTree.jsp> on Mar. 25, 2014.*

Bashshur et al., "TeleMedicine: A New Health Care Delivery System", Annual Reviews Public Health 21 (2000): pp. 613-637, 2000.*

Blumrosen et al., "New Wearable Body Sensor for Continuous Diagnosis of Internal Tissue Bleeding", In Proceedings of the 2009 Sixth International Workshop on Wearable and Implantable Body Sensor Networks, 5 pages, 2009.*

Gao et al., "Vital Signs Monitoring and Patient tracking Over a Wireless Network", In Proceedings of the 27th Annual International Conference of the IEEE EMBS, Shanghai, Sep. 2005, 4 pages.*

Hong et al., "A Wireless 3-Channel ECG Transmission System Using PDA Phone", 2007 International Conference on Convergence Information Technology, IEEE Computer Society, pp. 462-465, 2007.*

Milenkovic et al., "Wireless Sensor Networks for Personal Health Monitoring: Issues and an Implementation", Computer Communications 29 (2006): pp. 2521-2533, 2006.*

Morton et al., "Importance of Emergency Identification Schemes", Emergency Medicine Journal 2002; 19: pp. 584-586, 2002.*

Shin et al., "Ubiquitous House and Unconstrained Monitoring Devices for Home Healthcare System", In Proceedings of the 6th International Special Topic Conference on ITAB, 2007, Tokyo, pp. 201-204.*

K. Vanthournout et al., "A Taxonomy for Resource Discovery", PERS Ubiquit Comput 9, pp. 81-89, 2005.

C. Srisuwanrat et al., "Optimal Scheduling of Probabilistic Repetitive Projects Using Completed Unit and Genetic Algorithms", Proceedings of The 2007 Winter Simulation Conference, pp. 2151-2158, 2007.

S. Bharathi et al., "Scheduling Data-Intensive Workflows on Storage Constrained Resources", Works 09, Portland, OR, pp. 1-10 Nov. 15, 2009.

J. Redondo et al., "Solving the Multiple Competitive Facilities Location and Design Problem on the Plane", Massachusetts Institute of Technology, Evolutionary Computation, vol. 17, No. 1, pp. 21-53, 2009.

H. Van et al., "Autonomic Virtual Resource Management for Service Hosting Platforms", Cloud'09, pp. 1-8 , May 23, 2009.

U.S. Appl. No. 12/795,847, Specification filed Jun. 8, 2010.

U.S. Appl. No. 12/851,995—Non-Final Office Action mailed Apr. 25, 2012.

U.S. Appl. No. 12/851,995—Specification filed Aug. 6, 2010.

U.S. Appl. No. 12/903,376—Specification filed Oct. 13, 2010.

U.S. Appl. No. 12/875,261—Specification filed Sep. 3, 2010.

U.S. Appl. No. 12/884,665—Specification filed Sep. 17, 2010.

U.S. Appl. No. 12/875,261—Non-Final Office Action mailed Feb. 14, 2012.

U.S. Appl. No. 12/884,665—Non-Final Office Action mailed Apr. 11, 2012.

U.S. Appl. No. 12/903,376—Non-Final Office Action Mailed Jul. 30, 2012.

U.S. Appl. No. 12/875,261—Notice of Allowance Mailed Sep. 27, 2012.

Phillip E. Hayes et al., "Picking Up the Pieces: Utilizing Disaster Recovery Project Management to Improve Readiness and Response Time," IEEE Industry Applications Magazine, Nov./Dec. 2002, pp. 1-10 (Abstract).

Kun Wang et al., "A Mathematical Approach to Disaster Recovery Planning," Proceedings of The First International Conference on Semantics, Knowledge, and Grid, 2005, pp. 1-3 (Abstract).

E. A. Silver, "An Overview of Heuristic Solution Methods," The Journal of the Operational Research Society, vol. 55, No. 9, Sep. 2004, pp. 936-956 (Abstract).

Smith et al., "Collaborative Approaches to Research," HEFCE Fundamental Review of Research Policy and Planning, Final Report, Apr. 2000, pp. 1-117.

William E. Souder, "Analytical Effectiveness of Mathematical Models for R&D Project Selection," Management Science, vol. 19, No. 8, Application Seires, Apr. 1973, pp. 907-923 (Abstract).

J. Altmann et al., "Cooperative Software Development: Concepts, Model and Tools," Technology of Object-Oriented Languages and Systems, 1999, pp. 1-14.

(56) References Cited

OTHER PUBLICATIONS

Shou-Qi Cao et al., "Research on Resource Scheduling for Development Process of Complicated Product," Computer Supported Cooperative Work in Design, 2005. Proceedings of the Ninth International Conference on, vol. 1, pp. 229-233 (Abstract).

Ming Chen et al., "Research on Organization Method of Development Activities for Complicated Product," Computer Supported Cooperative Work in Design, 2005. Proceedings of The Ninth International Conference on, vol. 1, pp. 234-239 (Abstract).

Luckham et al., "Event Processing Glossary," Jul. 2008, pp. 1-19. http://complexevents.com.

Dept of Health and Human Services Agency for Healthcare Research and Quality, "AHRQ Quality Indicators—Patient Safety Indicators—Technical Specifications," 2012, pp. 1-149. http://www.qualityindicators.ahrq.gov.

Wong et al., "Rule-Based Anomaly Pattern Detection for Detecting Disease Outbreaks," AAAI-02 Proceedings, 2002, pp. 1-7.

Grzymala-Busse, "Knowledge Acquisition Under Uncertainty—A Rough Set Approach," Journal of Intelligent and Robotic Systems, 1988 (Abstract).

Schadow et al., "Discussion Paper: Privacy-Preserving Distributed Queries for a Clinical Case Research Network," IEE International Conference on Data Mining Workshop on Privacy, Security, and Data Mining, 2002 (Abstract).

T. Vercauteren et al., "Hierarchical Forecasting of Web Server Workload Using Sequential Monte Carlo Training", IEEE Transactions on Signal Processing, vol. 55, No. 4, pp. 1286-1297, Apr. 2007. (Abstract)

P. Palazzari et al., "Synthesis of Pipelined Systems for the Contemporaneous Execution of Periodic and Aperiodic Tasks with Hard Real-Time Constraints", 18th International Parallel and Distributed Processing Symposium, 121. IEEE Comput. Soc, Los Alamitos, CA, USA, 2004, pp. LVI-289 (Abstract).

RL Dillion et al., "Optimal use of Budget Reserves to Minimize Technical and Management Failure Risks During Complex Project Development", IEEE Transactions on Engineering Management, vol. 52, No. 3, pp. 382-395, Aug. 2005. (Abstract).

U.S. Appl. No. 12/884,665—Final Office Action Mailed Oct. 18, 2012.

U.S. Appl. No. 12/795,847—Non-Final Office Action Mailed Nov. 26, 2012.

U.S. Appl. No. 12/851,995—Final Office Action Mailed Nov. 8, 2012.

U.S. Appl. No. 12/903,376—Notice of Allowance Mailed Dec. 19, 2012.

U.S. Appl. No. 12/851,995—Examiner's Answer Mailed May 10, 2013.

U.S. Appl. No. 12/851,995—Supplemental Examiner's Answer Mailed May 22, 2013.

U.S. Appl. No. 12/884,665—Examiner's Answer Mailed May 16, 2013.

U.S. Appl. No. 12/795,847—Notice of Allowance Mailed Jun. 5, 2013.

\* cited by examiner

DIRECTING A USER TO A MEDICAL RESOURCE

The present application is a continuation-in-part application and claims the benefit of prior nonprovisional U.S. patent application Ser. No. 12/875,261, filed Sep. 3, 2010.

BACKGROUND

The present disclosure relates to the field of computers and physiological sensors, and specifically to the use of computers and physiological sensors in the field of medicine. Still more particularly, the present disclosure relates to the use of computers and physiological sensors in directing a user to a medical resource based on real-time readings from a physiological sensor that is in use on the user.

Medical resources provide high-tech to low-tech assistance to a person. For example, an operating room with the latest monitoring and surgical tools and personnel provides a high-tech solution to a person having a heart attack, while a park bench provides a low-tech solution to a person whose medical condition simply limits his stamina while walking.

SUMMARY

A processor-implemented method, system, and/or computer program product directs a user using a physiological sensor to a needed medical resource. A real-time state of a medical condition of a user is determined based on readings from a physiological sensor on a user. A processing system correlates the real-time state of the medical condition of the user to a medical resource, which has been predetermined to have a capability of ameliorating the real-time state of the medical condition of the user. Directions are then sent, to the user, for a temporally nearest medical resource that has been predetermined to have the capability of ameliorating the real-time state of the medical condition of the user.

DETAILED DESCRIPTION

Figure 1:
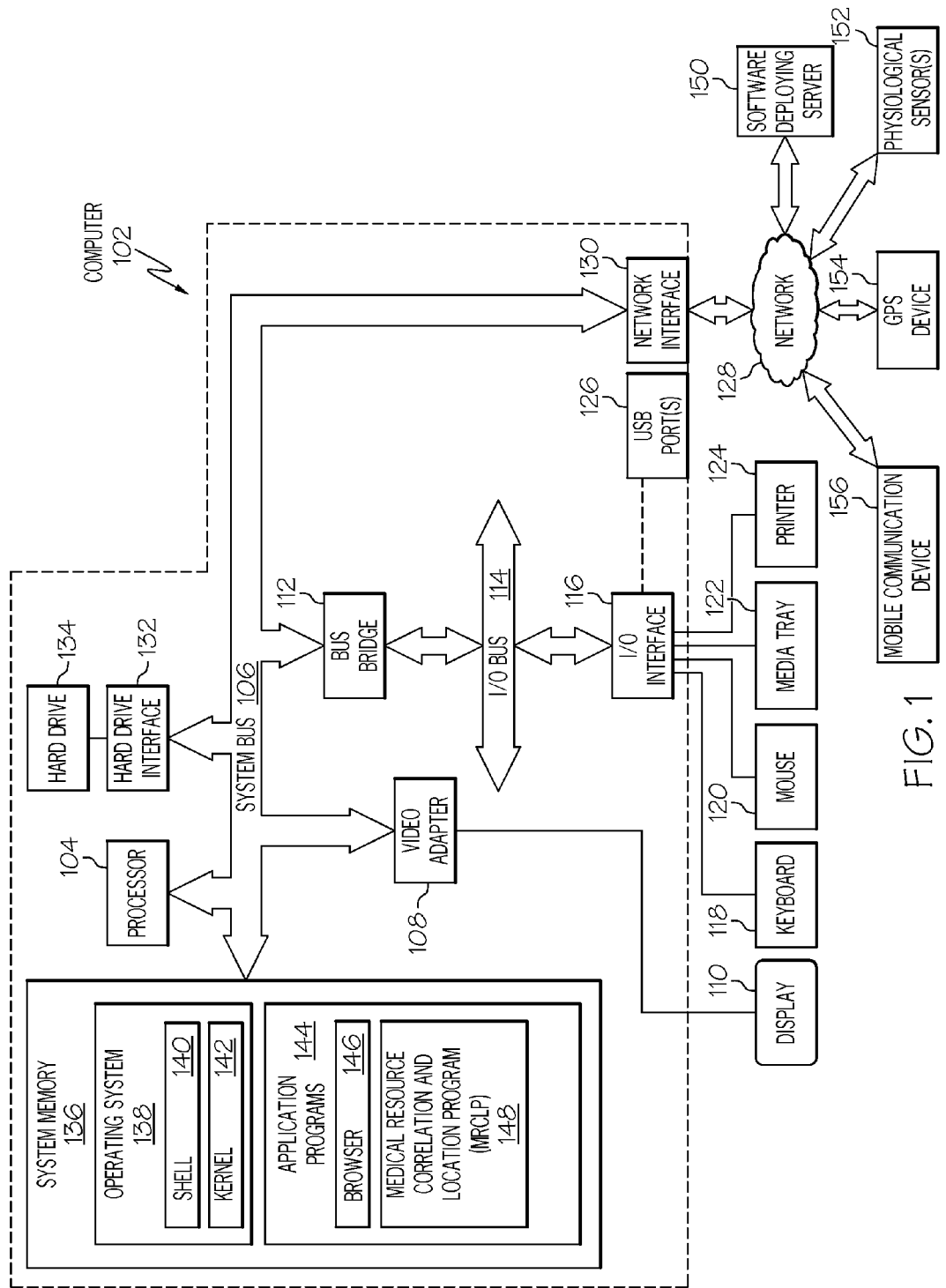
FIG. 1 depicts an exemplary computer in which the present disclosure may be implemented.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary computer 102, which may be utilized by the present invention. Note that some or all of the exemplary architecture, including both depicted hardware and software, shown for and within computer 102 may be utilized by software deploying server 150, physiological sensor(s) 152, a Global Positioning System (GPS) device 154, and/or mobile communication device 156 shown in FIG. 1, and/or local processing system 202 shown in FIG. 2.

Computer 102 includes a processing unit 104 that is coupled to a system bus 106. Processing unit 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a printer 124, and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 using a network interface 130. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (and, in one embodiment, software deploying server 150's system memory) also include a medical resource correlation and location program (MRCLP) 148. MRCLP 148 includes code for implementing the processes described below, including those described in FIGS. 2-3. In one embodiment, computer 102 is able to download MRCLP 148 from software deploying server 150, including in an on-demand basis, wherein the code in MRCLP 148 is not downloaded until needed for execution. Note further that, in one embodiment of the present invention, software deploying server 150 performs all of the functions associated with the present invention (including execution of MRCLP 148), thus freeing computer 102 from having to use its own internal computing resources to execute MRCLP 148.

The hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Figure 2:
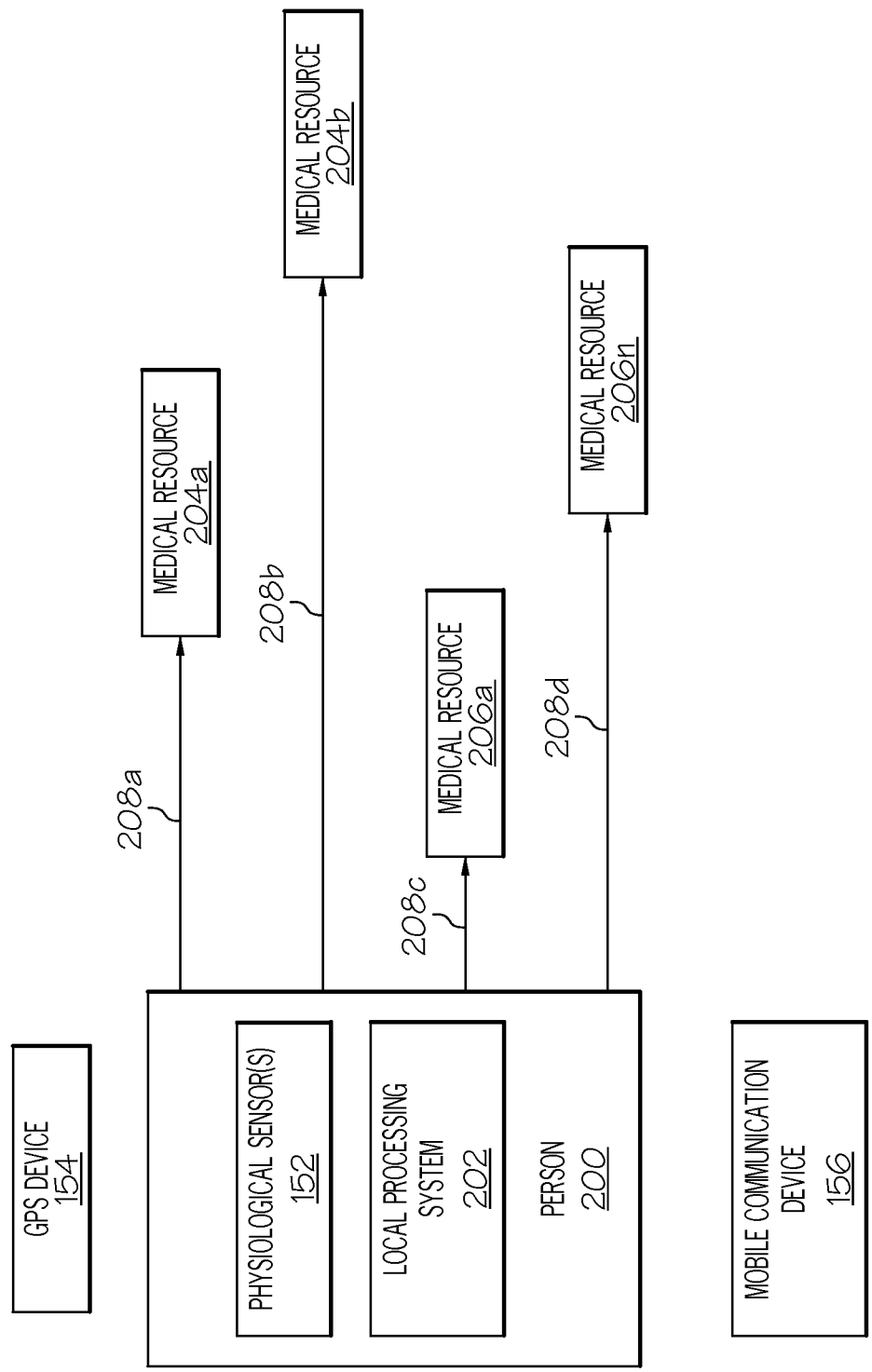
FIG. 2 depicts a relationship among a person, physiological sensors, and medical resources as contemplated in one embodiment of the present invention.

With reference now to FIG. 2, consider a user depicted as person 200, on whom are one or more physiological sensors 152. These one or more physiological sensors 152 are inside of, carried by, strapped to, or otherwise proximate to the person 200. For example, an oxygen saturation monitor is attached to a fingertip of the person 200; a portable electrocardiogram (ECG/EKG) machine, with leads attached to the person 200, is worn by the person 200 in a carry-pack; a continuous glucose monitoring device, having sensors attached to or under a patient's skin, is carried by person 200; a therapeutic drug monitoring device can be surgically implanted to remain inside the person 200; etc. Thus, the physiological sensors 152 are sensors that monitor physiological/pharmaceutical/medical/etc. conditions of person 200 to which the physiological sensors 152 are attached/worn/implanted/carried/etc.

In accordance with one embodiment of the present invention, the person 200 also carries (or otherwise has mobile access to) a GPS device 154 and/or a mobile communication device 156, which may be combined into a single device. That is, a mobile communication device 156 (e.g., a "smart" phone that is capable of connecting to the Internet, a cellular network, etc.) may be GPS-enabled, such that the real-time location of person 200 can always be determined. The GPS-enabled device utilizes signals from Global Positioning System (GPS) satellites to determine the real-time physical location (longitude, latitude, and altitude) of the person 200.

As described herein, when one or more of the physiological sensor(s) 152 detects a real-time state of a medical condition (of person 200) that warrants a medical resource, directions to the nearest appropriate medical resource are sent to the mobile communication device 156, based on information from the GPS device. For example, assume that person 200 is a diabetic who has taken too much insulin, or is chronically hypoglycemic. When readings from the physiological sensor (s) 152 indicate that person 200 is currently experiencing an excessively low blood glucose level, a processor (e.g., part of local processing system 202 or part of a remote system such as computer 102 shown in FIG. 1) correlates that condition with what type of medical resource is needed. In this example, the medical resource may be any type of vendor from which the person 200 can obtain a soft drink that, upon ingestion, will immediately bring the blood glucose level back up to healthy levels.

In the example shown in FIG. 2, the processor, based on information from a local or remote database and current real-time coordinates generated by the GPS device 154, identifies four medical resources, identified as medical resource 204*a* and medical resource 204*b* (where "b" is an integer), and medical resources 206*a*-n (where "n" is an integer). As indicated by distance arrow 208*c*, medical resource 206*a* is the closest medical resource to the person 200. However, medical resource 206*a* is not the right type of medical resource for a hypoglycemic patient. That is, soft drinks or similar substances are not available from medical resource 206*a*, which may be a clothing store. Thus, the processor ignores medical resource 206*a*. However, the processor identifies medical resource 204*a* and medical resource 204*b* as resources (e.g., convenience stores) where glucose-rich beverages are available. As represented by the length of distance arrow 208*a* compared to the length of distance arrow 208*b*, medical resource 204*a* is the closest medical resource that is able to ameliorate the current state of the medical condition (e.g., hypoglycemia) of the person 200. Note that medical resource 206*n* is not considered to be a viable medical resource candidate since 1) it is not the needed type of medical resource (i.e., does not sell soft drinks) and 2) it is farther away than medical resource 204*a*.

Once the processor has identified the temporally closest medical resource, directions to that medical resource are sent to the mobile communication device 156, allowing the person 200 to go directly to that needed medical resource. Note that the selected medical resource is temporally closest. Ordinarily, the temporally closest medical resource is the medical resource that is physically the closest. However, in some embodiments, a physically closest medical resource may actually take longer to get to than a more distant medical resource, and thus is not temporally closest. For example, street blockage, traffic accidents, lack of walkways/roadways, etc. may make is faster to get to a medical resource that is physically farther away from the person 200 than another medical resource. Note also that the person 200 may be a pedestrian, or may be a passenger in a vehicle, either private or public.

Figure 3:
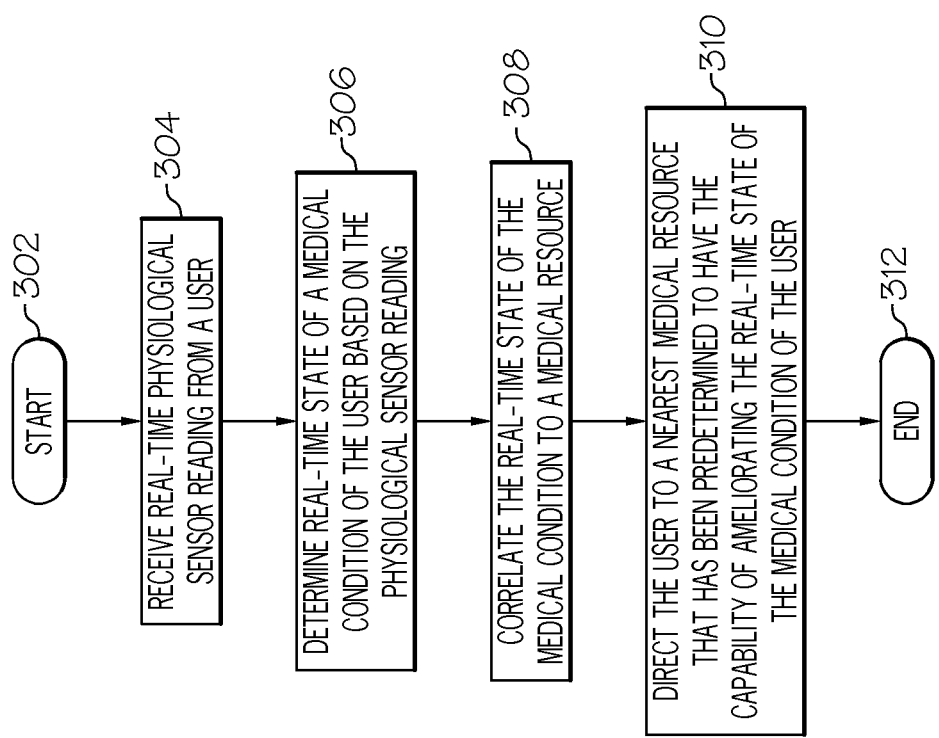
FIG. 3 is a high-level flow-chart of one or more actions performed by a processor to direct a user to an appropriate medical resource based on real-time readings of physiological sensor(s) on the user.

Consider now FIG. 3, which presents a high-level flow chart of one or more actions performed by a processor to direct a user to a temporally nearest medical resource based on real-time readings from physiological sensor(s) on the user. After initiator block 302, real-time physiological sensor readings are received from one or more physiological sensors on a user (block 304). The physiological sensor(s) may be worn by, attached to, implanted within, carried by, or otherwise positioned proximately to the user, thus enabling the taking of physiological measurements. These physiological measurements may be oxygen saturation levels in blood; glucose levels in blood; pharmaceutical levels in blood, urine, or exhaled breath; respiration levels (how many times a minute the person takes a breath); EKG readings, to include anomalies such as irregular heartbeats, both chronic and acute (including life-threatening); electroencephalogram (EEG) readings (i.e., from a portable EEG cap/monitor system); body temperature (e.g., from a skin sensor thermometer; an ingested "pill" thermometer to measure body core temperature; etc.); blood pressure readings; etc. Note that some or all of these physiological measurements may be of medical conditions that are imperceptible to the user. For example, a person may have a life-threatening anomaly in his heart rhythm, but will not "feel" anything unusual. An EKG sensor, however, will detect this anomaly, thus setting off the directions to the requisite medical resource, whether that be a simple bench to sit upon (thus allowing the heart to be under less stress) or a hospital (to provide emergency surgery, pharmaceuticals, etc.). Note that this imperceptible medical condition may be transient (i.e., exists in real-time for less than some predetermined length of time). Nonetheless, even though the event passes, the person may still need medical treatment. Without the real-time mobile monitoring however, the event would be ignored or never detected, since it may or may not re-manifest itself.

As described in block 306, based on the physiological sensor reading(s) received, the processor determines what the real-time state of the medical condition of the user is. For example, if the processor receives a sensor reading indicating low blood glucose, then the real-time state of the medical condition is hypoglycemia. If the processor receives a sensor reading indicating an irregular heartbeat, then the real-time state of the medical condition may be tachycardia. If the processor receives a sensor reading indicating an elevated body core temperature, then the real-time state of the medical condition may be heat exhaustion. If the processor receives a sensor reading indicating rapid shallow breathing, then the real-time state of the medical condition may be hyperventilation and/or hyperventilation-induced blood alkalosis. These examples are representative of the concept of how a real-time state of a medical condition of the user is determined based on readings from the physiological sensors on the user, and are not intended to limit the scope of the present invention.

As described in block 308, the real-time state of the medical condition (determined in block 306) is then correlated to a medical resource that has been predetermined to have the capability of ameliorating the real-time state of the medical condition of the user. This medical resource may be from a predetermined list of medical resources, which have been pre-qualified according to their capabilities/resources. For example, assume that a physiological sensor (e.g., an EKG, a respiration monitor, a thermometer, etc.) generates a reading that leads to the real-time state of the medical condition that the user is overexerting, based on some predefined "safe" parameters for that person. That is, if that person's heart rate goes over 160 beats per minute, or his respiration rate goes over 20 breaths per minute, or his core body temperature goes over 102° F., any or all of these have been predetermined as being unsafe for that person, and thus he is overexerted. In order to address this real-time state of his medical condition, certain types of medical resources have been predetermined as appropriate for ameliorating the real-time state of this medical condition. For example, a bench or similar seat has been predetermined as being adequate for ameliorating the real-time state of simply being overexerted. A nearest air-conditioned public building has been predetermined as being adequate for cooling down an overheated person. Professional medical care from a medical facility has been predetermined as being adequate for providing needed high-level medical treatment. A closest nutrition vendor has been predetermined as being appropriate for providing/selling fruit juice, soft drinks, energy bars, etc. needed by a person who is suffering from hypoglycemia. Whatever the real-time state of the medical condition, an appropriate predetermined type of medical resource, which may also be pre-approved and/or pre-selected according to specific locations of medical resources that match the requisite type of medical resource, is then correlated to that real-time state of the medical condition as being the appropriate type of medical resource for ameliorating the real-time state of the medical condition, whether that real-time state of the medical condition is perceptible or imperceptible to the user being monitored.

As described in block 310, directions are then issued (e.g., sent to a user's "smart" phone) to the user, directing him to a temporally closest medical resource that has been predetermined to have the capability of ameliorating the real-time state of the medical condition of the user. Note that in one embodiment, the temporally closest medical resource and the physically closest medical resource are the same. However, in another embodiment, the temporally closest medical resource may be physically farther away from the user than another medical resource. That is, descriptions of current travel conditions (i.e., blocked roads or traffic jams if the user is in a vehicle, blocked walkways or dangerously iced walkways if the user is a pedestrian, etc.) may be received by the processor that is correlating the real-time state of the medical condition to the medical resource. Thus, the current travel conditions may result in a different, perhaps farther away, medical resource being identified as being the temporally closest to the user, or alternatively may be the safest for the user to reach.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer program product for directing a user to a medical resource, the computer program product comprising a non-transitory computer readable storage medium having program code embodied therewith, wherein the program code, when read and executed by a processor, performs a method comprising:
   determining a real-time state of a medical condition of a user based on readings from one or more physiological sensors on the user;
   correlating the real-time state of the medical condition of the user to a medical resource by:
      identifying multiple medical resources as identified multiple medical resources;
      determining what type of medical product is provided by each of the identified medical resources;
      rejecting any of the identified multiple medical resources that do not provide a medical product that has been predetermined to have the capability of ameliorating the real-time state of the medical condition of the user;
      identifying any of the identified multiple medical resources, which do provide the medical product that has been predetermined to have the capability of ameliorating the real-time state of the medical condition of the user, as candidate medical resources for ameliorating the real-time state of the medical condition of the user;
   issuing, to the user, directions to a temporally closest candidate medical resource that has been identified and predetermined to have the capability of ameliorating the real-time state of the medical condition of the user by providing the medical product that has been predetermined to have the capability of ameliorating the real-time state of the medical condition of the user;

predetermining that a park bench has a capability of ameliorating an overexertion of the user, wherein the overexertion of the user is identified by the processor as a heartrate of the user exceeding a first predefined limit, a respiration rate of the user exceeding a second predefined limit, and a core body temperature of the user exceeding a third predefined limit;

in response to receiving a reading from the one or more physiological sensors indicating that the user is being overexerted, directing the user to a nearest park bench to ameliorate the overexertion of the user;

predetermining that any medical facility from a predetermined list of medical facilities has resources that are capable of ameliorating a first acute medical condition of the user;

in response to receiving a reading from the one or more physiological sensors indicating that the user is currently suffering from the first acute medical condition, directing the user to a temporally nearest medical facility from the predetermined list of medical facilities;

predetermining that a climate controlled room provides an environment that is capable of ameliorating a second acute medical condition of the user;

in response to receiving a reading from the one or more physiological sensors indicating that the user is currently suffering from the second acute medical condition, directing the user to a nearest climate controlled room;

predetermining that a nutrition vendor has resources capable of ameliorating a third acute medical condition of the user;

in response to receiving a reading from the one or more physiological sensors indicating that the user is currently suffering from the third acute medical condition, directing the user to a nearest nutrition vendor;

receiving a description of current travel conditions at a current location of the user;

identifying the temporally closest candidate medical resource based on travel time adjustments caused by the current travel conditions at the current location of the user;

receiving, from the one or more physiological sensors, a real-time state of an imperceptible medical condition of the user, wherein the imperceptible medical condition is detected by the one or more physiological sensors but is imperceptible to the user, wherein the imperceptible medical condition is a transient medical condition that exists in the user in real-time for less than predetermined length of time, wherein the user requires medical treatment related to the transient medical condition after the transient medical condition ceases, wherein the transient medical condition is a singular event that does not recur, and wherein detection of the singular event is a sole evidence of the transient medical condition;

correlating the real-time state of the imperceptible medical condition of the user to the medical resource, wherein the medical resource has been predetermined to have a capability of treating a cause of the real-time state of the imperceptible medical condition of the user;

defining a first limit for a heartrate of the user, a second limit for a respiration rate of the user, and a third limit for a core body temperature of the user, wherein the first limit, the second limit, and the third limit define safe parameters that are specific for the user;

detecting, based on readings from the one or more physiological sensors on the user, that the heartrate of the user is currently exceeding the first predefined limit, the respiration rate of the user is currently exceeding the second predefined limit, and the core body temperature of the user is currently exceeding the third predefined limit;

issuing, to the user, directions to a temporally closest candidate medical resource that has been identified and predetermined to have the capability of reducing the heartrate of the user below the first predefined limit, reducing the respiration rate of the user below the second predefined limit, and reducing the core body temperature of the user below the third predefined limit;

determining that the medical condition of the user is a transient medical condition, wherein the transient medical condition ceases within a predetermined length of time without medical treatment, wherein the transient medical condition is an irregular cardiac condition of the user, wherein the transient medical condition is imperceptible to the user, and wherein a bench is a medical resource that has been predetermined to have the capability of ameliorating the transient medical condition of the user;

issuing, to the user, directions to a temporally closest bench on which the user can sit during the transient medical condition;

identifying a first medical resource and a second medical resource as having the capability of ameliorating the real-time state of the medical condition of the user, wherein the first medical resource is physically farther from the user than the second medical resource;

determining that there is a lack of walkways between the user and the second medical resource;

determining that the first medical resource is the temporally closest medical resource based on the lack of walkways between the user and the second medical resource;

identifying the first medical resource and the second medical resource as having the capability of ameliorating the real-time state of the medical condition of the user, wherein the first medical resource is physically farther from the user than the second medical resource;

determining that walkways between the user and the second medical resource are currently iced over; and determining that the first medical resource is the temporally closest medical resource based on the iced over condition of walkways between the user and the second medical resource.

2. A method for directing a user to a medical resource, the method comprising:

determining, by one or more processors, a real-time state of a medical condition of a user based on readings from one or more physiological sensors on the user;

correlating, by the one or more processors, the real-time state of the medical condition of the user to a medical resource by:

identifying multiple medical resources as identified multiple medical resources;

determining what type of medical product is provided by each of the identified medical resources;

rejecting any of the identified multiple medical resources that do not provide a medical product that has been predetermined to have the capability of ameliorating the real-time state of the medical condition of the user;

identifying any of the identified multiple medical resources, which do provide the medical product that has been predetermined to have the capability of ameliorating the real-time state of the medical condition of the user, as candidate medical resources for ameliorating the real-time state of the medical condition of the user;

issuing, by the one or more processors and to the user, directions to a temporally closest candidate medical resource that has been identified and predetermined to have the capability of ameliorating the real-time state of the medical condition of the user by providing the medical product that has been predetermined to have the capability of ameliorating the real-time state of the medical condition of the user;

predetermining, by the one or more processors, that a park bench has a capability of ameliorating an overexertion of the user, wherein the overexertion of the user is identified by the one or more physiological sensors on the user as a heartrate of the user exceeding a first predefined limit, a respiration rate of the user exceeding a second predefined limit, and a core body temperature of the user exceeding a third predefined limit;

in response to receiving a reading from the one or more physiological sensors indicating that the user is being overexerted, directing, by the one or more processors, the user to a nearest park bench to ameliorate the overexertion of the user;

predetermining, by the one or more processors, that any medical facility from a predetermined list of medical facilities has resources that are capable of ameliorating a first acute medical condition of the user;

in response to receiving a reading from the one or more physiological sensors indicating that the user is currently suffering from the first acute medical condition, directing, by the one or more processors, the user to a temporally nearest medical facility from the predetermined list of medical facilities;

predetermining, by the one or more processors, that a climate controlled room provides an environment that is capable of ameliorating a second acute medical condition of the user;

in response to receiving a reading from the one or more physiological sensors indicating that the user is currently suffering from the second acute medical condition, directing, by the one or more processors, the user to a nearest climate controlled room;

predetermining, by the one or more processors, that a nutrition vendor has resources capable of ameliorating a third acute medical condition of the user;

in response to receiving a reading from the one or more physiological sensors indicating that the user is currently suffering from the third acute medical condition, directing, by the one or more processors, the user to a nearest nutrition vendor;

receiving, by the one or more processors, a description of current travel conditions at a current location of the user;

identifying, by the one or more processors, the temporally closest candidate medical resource based on travel time adjustments caused by the current travel conditions at the current location of the user;

receiving, by the one or more processors and from the one or more physiological sensors, a real-time state of an imperceptible medical condition of the user, wherein the imperceptible medical condition is detected by the one or more physiological sensors but is imperceptible to the user, wherein the imperceptible medical condition is a transient medical condition that exists in the user in real-time for less than predetermined length of time, wherein the user requires medical treatment related to the transient medical condition after the transient medical condition ceases, wherein the transient medical condition is a singular event that does not recur, and wherein detection of the singular event is a sole evidence of the transient medical condition;

correlating, by the one or more processors, the real-time state of the imperceptible medical condition of the user to the medical resource, wherein the medical resource has been predetermined to have a capability of treating a cause of the real-time state of the imperceptible medical condition of the user;

defining, by the one or more processors, a first limit for a heartrate of the user, a second limit for a respiration rate of the user, and a third limit for a core body temperature of the user, wherein the first limit, the second limit, and the third limit define safe parameters that are specific for the user;

detecting, by the one or more processors and based on readings from the one or more physiological sensors on the user, that the heartrate of the user is currently exceeding the first predefined limit, the respiration rate of the user is currently exceeding the second predefined limit, and the core body temperature of the user is currently exceeding the third predefined limit;

issuing, by the one or more processors and to the user, directions to a temporally closest candidate medical resource that has been identified and predetermined to have the capability of reducing the heartrate of the user below the first predefined limit, reducing the respiration rate of the user below the second predefined limit, and reducing the core body temperature of the user below the third predefined limit;

determining, by the one or more processors and based on readings from the one or more physiological sensors, that the medical condition of the user is a transient medical condition, wherein the transient medical condition ceases within a predetermined length of time without medical treatment, wherein the transient medical condition is an irregular cardiac condition of the user, wherein the transient medical condition is imperceptible to the user, and wherein a bench is a medical resource that has been predetermined to have the capability of ameliorating the transient medical condition of the user;

issuing, by the one or more processors and to the user, directions to a temporally closest bench on which the user can sit during the transient medical condition;

identifying, by the one or more processors, a first medical resource and a second medical resource as having the capability of ameliorating the real-time state of the medical condition of the user, wherein the first medical resource is physically farther from the user than the second medical resource;

determining, by the one or more processors, that there is a lack of walkways between the user and the second medical resource;

determining, by the one or more processors, that the first medical resource is the temporally closest medical resource based on the lack of walkways between the user and the second medical resource;

identifying, by the one or more processors, the first medical resource and the second medical resource as having the capability of ameliorating the real-time state of the medical condition of the user, wherein the first medical resource is physically farther from the user than the second medical resource;

determining, by the one or more processors, that walkways between the user and the second medical resource are currently iced over; and determining, by the one or more processors, that the first medical resource is the temporally closest medical resource based on the iced over condition of walkways between the user and the second medical resource.

3. A computer system comprising:

a processor, a computer readable memory, and a non-transitory computer readable storage media, wherein the non-transitory computer readable storage medium has program code embodied therewith, and wherein the program code, when read and executed by the processor, performs a method comprising:

determining a real-time state of a medical condition of a user based on readings from one or more physiological sensors on the user;

correlating the real-time state of the medical condition of the user to a medical resource by:
  identifying multiple medical resources as identified multiple medical resources;
  determining what type of medical product is provided by each of the identified medical resources;
  rejecting any of the identified multiple medical resources that do not provide a medical product that has been predetermined to have the capability of ameliorating the real-time state of the medical condition of the user;
  identifying any of the identified multiple medical resources, which do provide the medical product that has been predetermined to have the capability of ameliorating the real-time state of the medical condition of the user, as candidate medical resources for ameliorating the real-time state of the medical condition of the user;

issuing, to the user, directions to a temporally closest candidate medical resource that has been identified and predetermined to have the capability of ameliorating the real-time state of the medical condition of the user by providing the medical product that has been predetermined to have the capability of ameliorating the real-time state of the medical condition of the user;

predetermining that a park bench has a capability of ameliorating an overexertion of the user, wherein the overexertion of the user is identified by the one or more physiological sensors on the user as a heartrate of the user exceeding a first predefined limit, a respiration rate of the user exceeding a second predefined limit, and a core body temperature of the user exceeding a third predefined limit;

in response to receiving a reading from the one or more physiological sensors indicating that the user is being overexerted, directing the user to a nearest park bench to ameliorate the overexertion of the user;

predetermining that any medical facility from a predetermined list of medical facilities has resources that are capable of ameliorating a first acute medical condition of the user;

in response to receiving a reading from the one or more physiological sensors indicating that the user is currently suffering from the first acute medical condition, directing the user to a temporally nearest medical facility from the predetermined list of medical facilities;

predetermining that a climate controlled room provides an environment that is capable of ameliorating a second acute medical condition of the user;

in response to receiving a reading from the one or more physiological sensors indicating that the user is currently suffering from the second acute medical condition, directing the user to a nearest climate controlled room;

predetermining that a nutrition vendor has resources capable of ameliorating a third acute medical condition of the user;

in response to receiving a reading from the one or more physiological sensors indicating that the user is currently suffering from the third acute medical condition, directing the user to a nearest nutrition vendor;

receiving a description of current travel conditions at a current location of the user;

identifying the temporally closest candidate medical resource based on travel time adjustments caused by the current travel conditions at the current location of the user;

receiving, from the one or more physiological sensors, a real-time state of an imperceptible medical condition of the user, wherein the imperceptible medical condition is detected by the one or more physiological sensors but is imperceptible to the user, wherein the imperceptible medical condition is a transient medical condition that exists in the user in real-time for less than predetermined length of time, wherein the user requires medical treatment related to the transient medical condition after the transient medical condition ceases, wherein the transient medical condition is a singular event that does not recur, and wherein detection of the singular event is a sole evidence of the transient medical condition;

correlating the real-time state of the imperceptible medical condition of the user to the medical resource, wherein the medical resource has been predetermined to have a capability of treating a cause of the real-time state of the imperceptible medical condition of the user;

defining a first limit for a heartrate of the user, a second limit for a respiration rate of the user, and a third limit for a core body temperature of the user, wherein the first limit, the second limit, and the third limit define safe parameters that are specific for the user;

detecting, based on readings from the one or more physiological sensors on the user, that the heartrate of the user is currently exceeding the first predefined limit, the respiration rate of the user is currently exceeding the second predefined limit, and the core body temperature of the user is currently exceeding the third predefined limit;

issuing, to the user, directions to a temporally closest candidate medical resource that has been identified and predetermined to have the capability of reducing the heartrate of the user below the first predefined limit, reducing the respiration rate of the user below the second predefined limit, and reducing the core body temperature of the user below the third predefined limit;

determining, based on readings from the one or more physiological sensors, that the medical condition of the user is a transient medical condition, wherein the transient medical condition ceases within a predetermined length of time without medical treatment, wherein the transient medical condition is an irregular cardiac condition of the user, wherein the transient medical condition is imperceptible to the user, and wherein a bench is a medical resource that has been predetermined to have the capability of ameliorating the transient medical condition of the user;

issuing, to the user, directions to a temporally closest bench on which the user can sit during the transient medical condition;

identifying a first medical resource and a second medical resource as having the capability of ameliorating the real-time state of the medical condition of the user, wherein the first medical resource is physically farther from the user than the second medical resource;
determining that there is a lack of walkways between the user and the second medical resource;
determining that the first medical resource is the temporally closest medical resource based on the lack of walkways between the user and the second medical resource;
identifying the first medical resource and the second medical resource as having the capability of ameliorating the real-time state of the medical condition of the user, wherein the first medical resource is physically farther from the user than the second medical resource;
determining that walkways between the user and the second medical resource are currently iced over; and
determining that the first medical resource is the temporally closest medical resource based on the iced over condition of walkways between the user and the second medical resource.

* * * * *